(12) United States Patent  (10) Patent No.: US 7,931,604 B2
Even Zohar et al.  (45) Date of Patent: Apr. 26, 2011

(54) METHOD FOR REAL TIME INTERACTIVE VISUALIZATION OF MUSCLE FORCES AND JOINT TORQUES IN THE HUMAN BODY

(75) Inventors: Oshri Even Zohar, Amsterdam (NL); Antonie J van den Bogert, Cleveland Heights, OH (US)

(73) Assignee: Motek B.V., Amsterdam (NL)

( * ) Notice: Subject to any disclaimer, the term of this patent is extended or adjusted under 35 U.S.C. 154(b) by 60 days.

(21) Appl. No.: 12/251,688

(22) Filed: Oct. 15, 2008

(65) Prior Publication Data

US 2009/0082701 A1     Mar. 26, 2009

Related U.S. Application Data

(63) Continuation of application No. 11/832,726, filed on Aug. 2, 2007, now abandoned.

(60) Provisional application No. 60/893,394, filed on Mar. 7, 2007.

(51) Int. Cl.
| | |
|---|---|
| A61B 5/103 | (2006.01) |
| A61B 5/117 | (2006.01) |
| G09G 5/00 | (2006.01) |
| G06T 13/00 | (2006.01) |
| G06T 15/70 | (2006.01) |
| G06K 9/00 | (2006.01) |
| G06F 7/60 | (2006.01) |
| G06F 17/00 | (2006.01) |

(52) U.S. Cl. ........ 600/595; 600/587; 345/156; 345/473; 382/107; 703/2

(58) Field of Classification Search .................. 345/156, 345/473; 382/107, 111; 600/595, 587; 703/2
See application file for complete search history.

(56) References Cited

U.S. PATENT DOCUMENTS

| | | | | |
|---|---|---|---|---|
| 5,623,428 | A | * | 4/1997 | Kunii et al. .................... 703/6 |
| 5,623,944 | A | | 4/1997 | Nashner |
| 5,625,577 | A | | 4/1997 | Kunii et al. |
| 5,791,351 | A | * | 8/1998 | Curchod ...................... 600/595 |
| 5,826,578 | A | * | 10/1998 | Curchod ...................... 600/595 |
| 5,872,858 | A | * | 2/1999 | Kamada et al. ............... 382/107 |
| 5,904,484 | A | * | 5/1999 | Burns .......................... 434/252 |
| 5,930,741 | A | * | 7/1999 | Kramer ........................ 702/153 |
| 5,937,081 | A | * | 8/1999 | O'Brill et al. ................. 382/111 |
| 6,102,832 | A | * | 8/2000 | Tani ................................ 482/4 |
| 6,119,516 | A | * | 9/2000 | Hock ......................... 73/379.01 |
| 6,738,065 | B1 | | 5/2004 | Even-Zohar |
| 6,774,885 | B1 | | 8/2004 | Even-Zohar |
| 7,136,722 | B2 | | 11/2006 | Nakamura et al. |

(Continued)

OTHER PUBLICATIONS

PCT Search Report dated Aug. 27, 2008 of Patent Application No. PCT/US08/54239 filed Feb. 19, 2008.

(Continued)

*Primary Examiner* — Max Hindenburg
*Assistant Examiner* — Sean P Dougherty
(74) *Attorney, Agent, or Firm* — Vern Maine & Associates

(57) ABSTRACT

A method and system are provided for the visual display of anatomical forces, that system having: a motion capture system; a computer, receiving data from said motion capture system; and a computational pipeline disposed on said computer; that computational pipeline being configured to calculate muscle forces and joint torques in real time and visually display those forces and torques.

10 Claims, 9 Drawing Sheets
(6 of 9 Drawing Sheet(s) Filed in Color)

U.S. PATENT DOCUMENTS

| | | | |
|---|---|---|---|
| 7,292,151 B2 * | 11/2007 | Ferguson et al. | 340/573.1 |
| 7,308,826 B2 * | 12/2007 | Nakamura et al. | 73/379.01 |
| 7,554,549 B2 * | 6/2009 | Sagar et al. | 345/473 |
| 7,573,477 B2 * | 8/2009 | Ng-Thow-Hing | 345/473 |
| 2002/0045517 A1 | 4/2002 | Oglesby et al. | |
| 2004/0256754 A1 | 12/2004 | Koguchi | |
| 2006/0135883 A1 | 6/2006 | Jonsson et al. | |
| 2006/0206215 A1 | 9/2006 | Clausen et al. | |
| 2006/0247904 A1 * | 11/2006 | Dariush | 703/11 |
| 2007/0172797 A1 * | 7/2007 | Hada et al. | 434/1 |
| 2008/0009771 A1 * | 1/2008 | Perry et al. | 600/587 |
| 2008/0180448 A1 * | 7/2008 | Anguelov et al. | 345/475 |
| 2009/0135189 A1 * | 5/2009 | Kim et al. | 345/473 |

OTHER PUBLICATIONS

McLean, Scott G. et al., "Sagittal Plane Biomechanics Cannot Injure the ACL During Sidestep Cutting", Clinical Biomechanics, 2004, pp. 828-838, Elsevier Ltd.

De Leva, Paolo, "Adjustments to Zatsiorsky-Seluyanov's Segment Inertia Parameters", J. Biomechanics, 1996, pp. 1223-1230, vol. 29, No. 9, Elsevier Science Ltd., Great Britain.

Delp, Scott L. et al., "An Interactive Graphics-Based Model of the Lower Extremity to Study Orthopedic Surgical Procedures", IEEE Transactions on Biomedical Engineering, Aug. 1990, pp. 757-767, vol. 37, No. 8.

Van Den Bogert, Antonie J. et al., "A Weighted Least Squares Method for Inverse Dynamic Analysis", Computer Methods in Biomechanics and Biomedical Engineering, 2007, pp. 1-7, vol. 00, No. 0.

Xia, Youshen et al., "An Improved Neural Network for Convex Quadratic Optimization with Application to Real-Time Beamforming", Neurocomputing, 2005, pp. 359-374, Elsevier B.V.

Van Der Helm, F.C.T., "A Finite Element Musculoskeletal Model of the Shoulder Mechanism", J. Biomechanics, 1994, pp. 551-569, vol. 27, No. 5, Elsevier Science Ltd, Great Britain.

"Nonlinear Models", Cambridge University Press, 1986-1992, pp. 675-684.

Rule 132 Declaration for Itzhak Siev-Ner, MD for U.S. Appl. No. 11/832,726, 4 pages.

PCT Search Report dated Jan. 16, 2009 for PCT Application No. PCT/IB08/01835 filed May 5, 2008.

* cited by examiner

METHOD FOR REAL TIME INTERACTIVE VISUALIZATION OF MUSCLE FORCES AND JOINT TORQUES IN THE HUMAN BODY

RELATED APPLICATIONS

This application is a continuation of U.S. application Ser. No. 11/832,726, filed Aug. 2, 2007, which claims the benefit of U.S. Provisional Applications No. 60/893,394, filed Mar. 7, 2007. This application is herein incorporated in its entirety by reference.

FIELD OF THE INVENTION

This invention most generally relates to a system that combines motion capture technology and a 3D computational musculoskeletal model to create a real time display environment where muscle forces and joint torques are illustrated. More specifically, various embodiments of the present invention create real time visualizations of the physical muscle forces and joint torques in the body during movement.

BACKGROUND OF THE INVENTION

Currently there is no known system or method available for visualizing in 3D the muscle forces exerted by the human body in real time. Most rehabilitation clinics and medical research institutes use specialized therapeutic programs, based on cause related classifications of movement disorders, but there is no known way that they can view the body force arrays in real time as it usually takes many hours and days of calculations to derive those parameters and the results are numerical or graphical and not intuitive to the viewer.

Motion Capture is a term for a variety of techniques, and the technology has existed for many years in a variety of applications. The aim of motion capture is to create three-dimensional (3D) animation and natural simulations in a performance oriented manner. In the entertainment industry, motion capture allows an operator to use computer-generated characters. Motion capture can be used to create complex motion, using the full range of human movements and allow also inanimate objects to move realistically. Some motion capture systems provide real-time feedback of the data and allow the operator to immediately determine whether the motion works sufficiently. Motion capture can be applied to full body motion as well as to hand animation, facial animation and real time lip sync. Motion capture is also used in medical, simulation, engineering and ergonomic applications, and in feature films, advertising, TV and 3D computer games.

Kinematics is the process of calculating the position in space of the end of a linked structure, given the angles of all the joints. Inverse Kinematics does the reverse. Given the end point of the structure, it calculates the angles of the joints needed to be in to achieve that end point. This process is used in robotics, 3D computer animation and some engineering applications.

Dynamics is the process of calculating the accelerations of a linked structure in space, given the set of internal and external forces acting on the structure. Inverse dynamics does the opposite. Given the accelerations of the structure, and a set of measured forces, it calculates the unknown internal forces needed to produce those accelerations. The result is typically provided as a set of joint torques and resultant joint forces.

What is needed, therefore, are techniques for creating a single computational pipeline of all the described steps in real time. Creating for the first time the capability to view muscle forces as they occur.

SUMMARY OF THE INVENTION

One embodiment of the present invention provides a method for real time display of the array of muscle forces and joint torques in a human body using color space animation of a 3D human body muscle model. Data stream coming from a motion capture system is parsed through a pipeline of specially written algorithms that derives joint orientations, accelerations and velocities and forward and inverse dynamics resulting in real time measurements of muscle forces and joint torques. Those are passed in real time to a 3D human muscle model making the forces and torques visible to the user as they happen.

Another embodiment of the present invention provides runtime interaction by a user or operator.

A further embodiment of the present invention provides a combination of motion capture technologies, simulation technology and custom real time data processing algorithms, using a combination of hardware and software elements combined with the authoring and control software to customize the visualization in real time of forces and torques exerted by the human body.

Still another embodiment of the invention creates a new measurement and visualization tool, bearing applications in various industries. The invention creates the possibility of looking at muscle force transference in the body for determining, registering and evaluating human functional performance to a range of given situations.

Yet another embodiment of the present invention provides a new measurement and visualization tool, bearing applications in various industries. The invention creates the possibility of looking at muscle forces and joint forces transference in the body for determining, registering and evaluating human functional performance to a range of given situations. Other applications include orthopedic and ergonomic studies and designs.

A yet further embodiment of the present invention provides a process that incorporates real time 3D marker data streams coming from a motion capture system through real-time sets of algorithms that derive from the 3D markers cloud the joints centers of rotation, positions and orientations, then derives accelerations and velocities and converts those into an array of muscle forces that are passed to the 3D human body muscle model as a data stream used in the 3D color space visualization of the muscle forces and joint torques.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
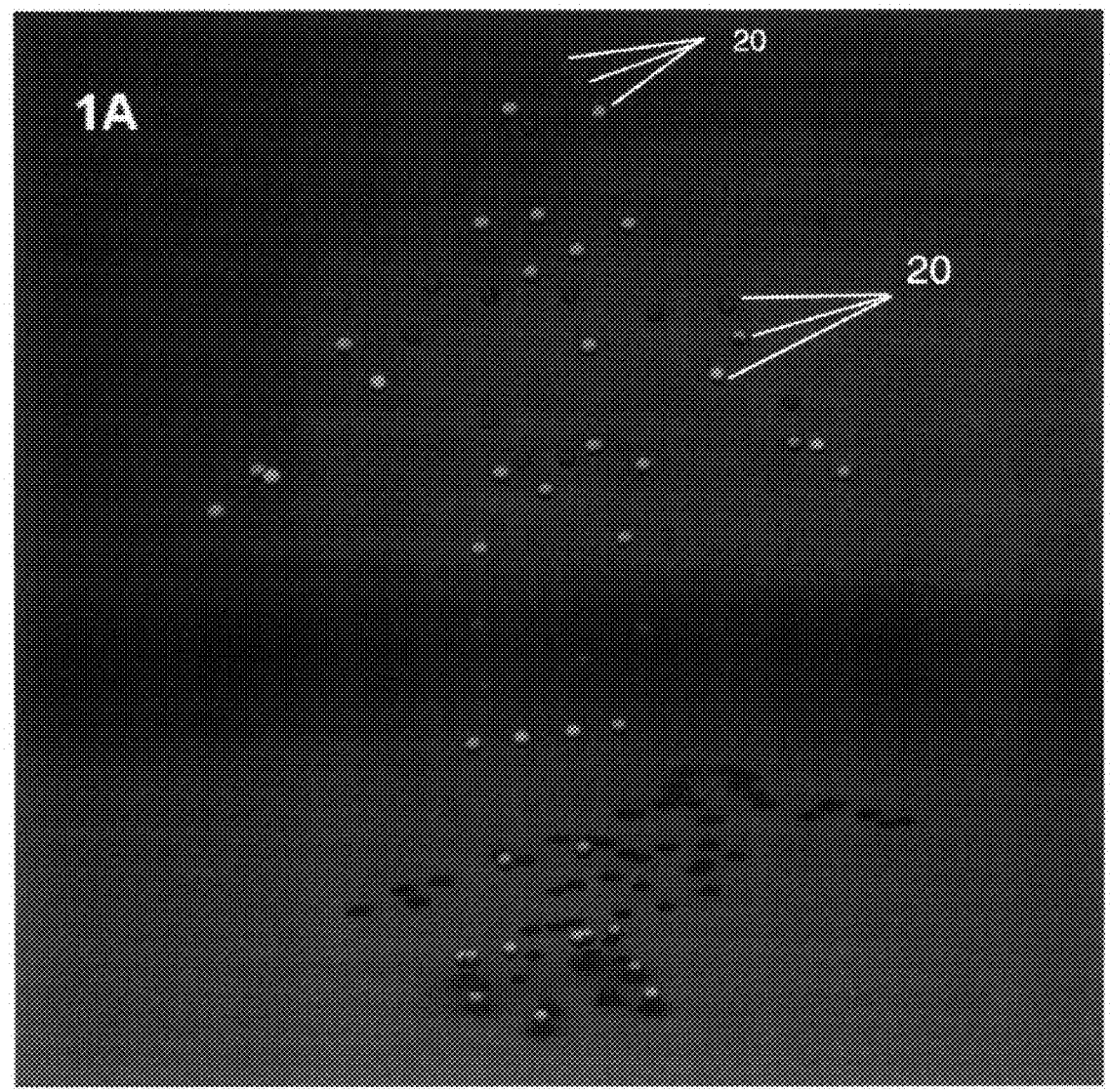
FIG. 1A is a computer generated image illustrating in a three dimensional representation the motion capture points disposed on a user (not shown) configured in accordance but not limited to one embodiment of the present invention.
Figure 1B:
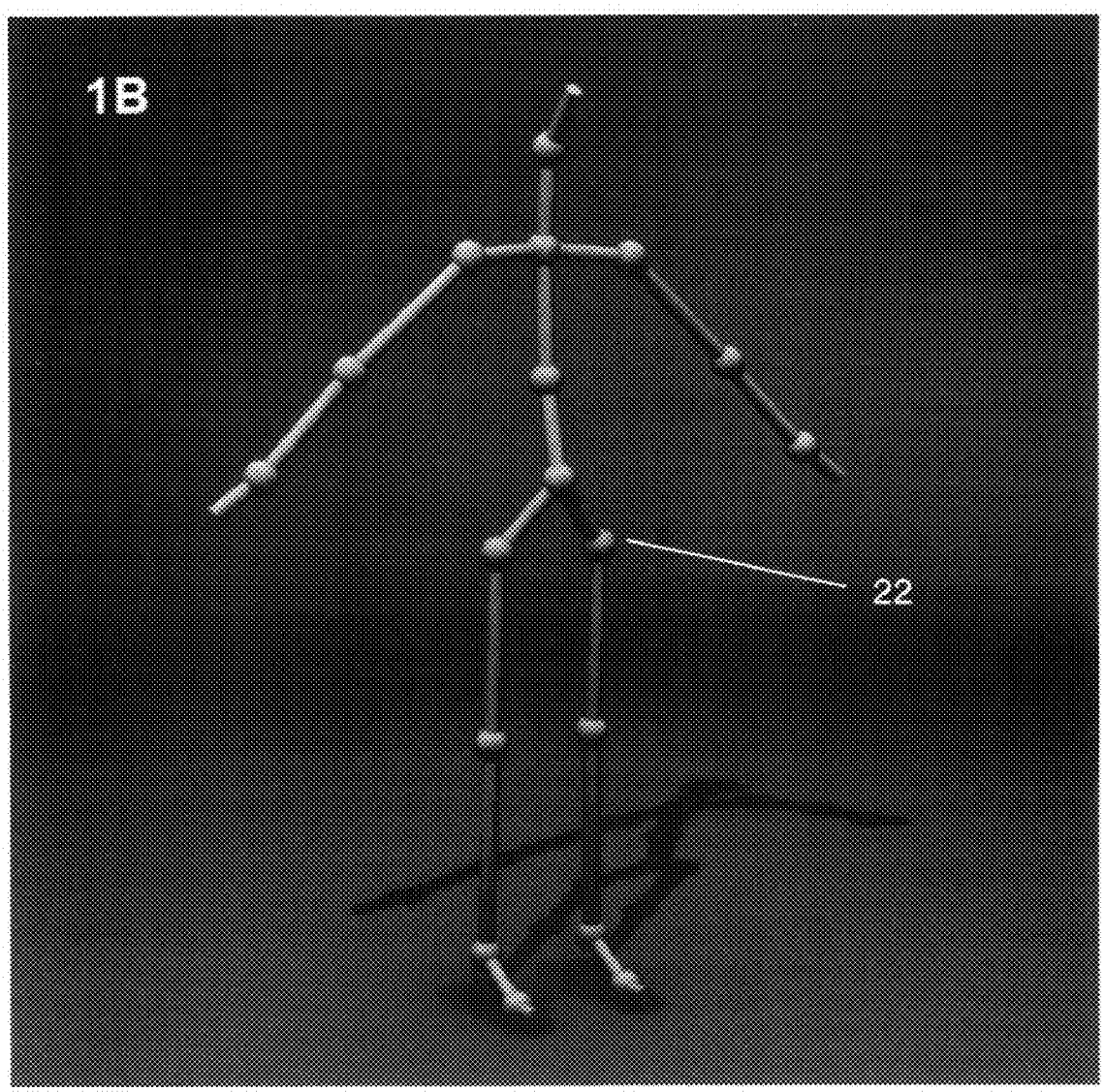
FIG. 1B is a computer generated image illustrating a kinematics skeleton configured in accordance with one embodiment of the present invention derived from the same motion capture points data as FIG. 1.

Muscle forces are typically invisible by nature and one can normally only see the results of applied muscle forces on the individual's surroundings. One embodiment of the present invention makes it possible to view simulated muscle forces in the human body in real-time, in a way that makes clear the force transference in the human musculoskeletal system. The process of achieving this functionality relies on fast and accurate real time motion capture data processing into an IK (inverse kinematics) skeletal layer containing joint positions and orientations, a further process deriving accelerations and velocities, a further process deriving inverse dynamics in real time, a further process deriving muscle forces from joint torques, and a final process converting the result streams into 3D visualizations of color and form changes in a 3D accurate human body muscle model.

The applicant herein incorporates by reference U.S. Pat. No. 6,774,885 for all purposes.

One embodiment of the invention is a method for real time display of the array of muscle forces and joint torques in a human body using color space animation of a 3D human body muscle model. Data streams coming from a motion capture system are parsed through a pipeline of specially written algorithms that derives joint orientations, accelerations and velocities and forward and inverse dynamics resulting in real time measurements of muscle forces and joint torques. Those are passed in real time to a 3D human muscle model making the forces and torques visible to the eye as they happen.

One embodiment of the present invention allows runtime interaction by a user or operator. Such an embodiment of the invention can be seen as a combination of motion capture technologies, simulation technology and custom real time data processing algorithms, using a combination of hardware and software elements combined with the authoring and control software to visualize in real time the forces and torques exerted by the human body.

One embodiment of the invention provides a new measurement and visualization tool, bearing applications in various industries. One embodiment of the invention creates the possibility of looking at muscle force transference in the body for determining, registering and evaluating human functional performance to a range of given situations. Although at least one embodiment of the present invention is intended for medical applications, embodiments of the present invention are adaptable for other market segments including ergonomics and sports.

Various embodiments of the present invention provide tools that are useful in numerous applications, including the sports and fitness industries. This system allows the visualizations of muscle forces for any given exercise in real-time. Such a system, illustrated in FIG. 3 can be used to enhance, optimize and improve muscle forces, by providing a realistic real time visualization of the given forces and torques. The system allows the user 30 to see the force transference to various muscles in the body and achieve the desired effect. A motion capture system 32 instantly records the user's motion and provides immediate muscle force visualizations 34.

One embodiment of the present invention may be utilized by the medical community by making it possible to view muscle forces and torques in real-time. It can assist and improve the quality of life of many patients and allow the perception of physical movement and muscle behaviors for those not otherwise capable of such motion. The system may be useful for victims of traumatic brain injury, cerebral damage, and spinal damage. The study of motion recognition supports the notion that the body remembers certain movements and can even regenerate synoptic paths. By visualizing the desired muscle force, the body can be re-trained to make that movement. In the field of orthopedics and prosthetics, embodiments of the present invention can assist patients in understanding their present situation, where they lack muscle force and where they are exerting too much force for compensation reasons. With orthopedics, prosthetics, and amputees, the system can visualize and track muscle deficiencies while training and improving movements.

Yet another embodiment of the present invention combines muscle forces and resultant joint force into a calculation and visualization of the forces acting within joints. This is useful as a training tool to prevent and treat overuse injuries in the workplace, in ergonomics and in sports.

Figure 2:
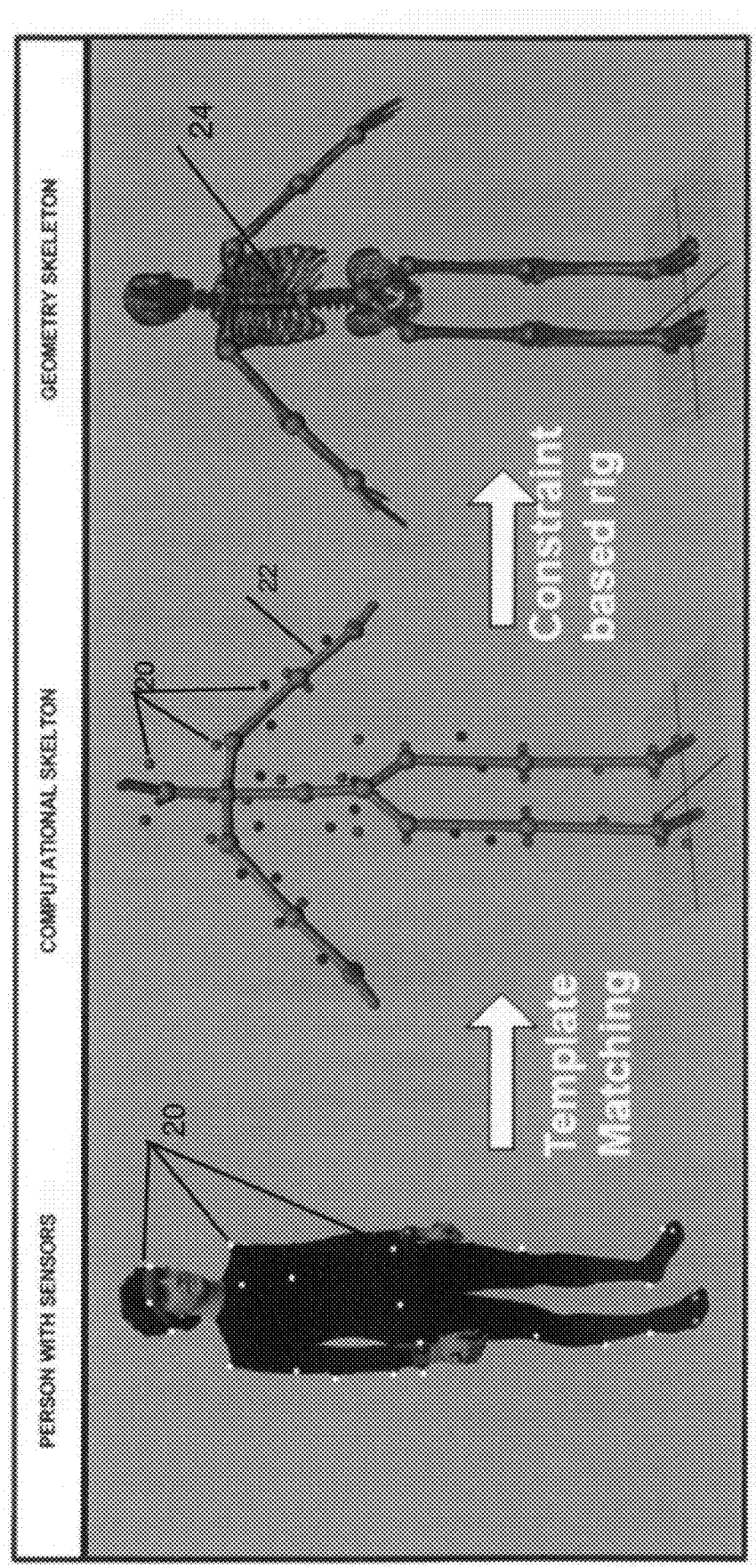
FIG. 2 is a computer generated image illustrating pipeline layer connections for processing the capture point data of a person with sensors and template matching it from a lookup table to generate a computational skeleton from which is derived a geometry skeleton configured in accordance with one embodiment of the present invention.

In the context of one embodiment of the present invention it is a first step in the data analysis pipeline illustrated in FIG. 2, taking the data stream from the motion capture system and calculating the joint angles for every body part, each joint calculated is drawn as a sphere in this drawing. In one embodiment of the present invention, Inverse kinematics is used to calculate the joint orientation from the motion capture data before deriving the accelerations and velocities of every body part. The next step in the pipeline is to take the calculated joint angles and to derive values of accelerations and velocities for every joint (representing every body part), the acceleration and velocities values are the base for calculating through the use of inverse dynamics, the muscle forces and joint torques which are then passed to the 3D muscle model display as color information.

One embodiment of the present invention in relation to medical applications can serve as an example. A development project called "Virtual Gait Lab" is one embodiment of the system operating in the real-time domain. Such an embodiment pertains to the development of a virtual reality system in which the muscle forces and joint torques of the human body can be seen and evaluated in real time in a variety of reproducible conditions.

Among the features of such an embodiment is the ability to enhance diagnostic and therapeutic activities in a range of medical fields. The enhancements are defined by allowing a medical expert team for the first time the opportunity to view and analyze muscle forces and joint torques patterns as they happen in a controlled real-time environment.

Such a system consists of a combination of an instrumented treadmill that is capable of measuring ground reaction forces, a large screen or projection system for the display of the forces, real time motion capture system and the custom computational pipeline translating the capture data to muscle forces and joint torques display.

An embodiment of the present invention seeks to develop an interactive virtual real-time muscle model, which can provide patients with means of almost unlimited exploratory behaviors and at the same time provide medical experts accurate measurement tools for monitoring the complex array of forces present in the human body.

Especially in complex balance tasks, the patterns of muscle activation determine whether a subject falls or not. These simulations are aimed at an understanding of normal or pathological response patterns in certain balance tasks.

Such an embodiment offers not only a test and learning environment for patients and doctors, but is also a valuable research environment for motor control. Such an embodiment opens the door to a new type of experiments in which real time muscle force visualization can be offered.

For example the muscle force tremors as observed in Parkinson patients are considered to be an enigma by many clinicians and human movement scientists. In these patients some visual cues are sufficient to trigger rather normal looking muscle force patterns (for instance used in walking), while in the absence of such stimuli a pattern can not even be started. In healthy subjects, the continuous control of muscle force transference during walking is possible by having a multi-channel sensory input onto a vast library of learned motor patterns. Once the possibility exists to view in real time the muscle force pattern immergence, it will lead to fundamental improvement in the understanding and possible treatment of the sickness. Such an embodiment will allow a new glimpse into the complexity of the natural processes associated with human motion.

Other examples can be found among patients with peripheral disorders, such as partial paralysis or paresis of a limb. In these situations, gait and balance are compromised both by a partial lack of sensory input and a lack of muscle coordination. The usual result of that is that in order to obtain a functional gait and balance the patients find compensations, resulting in deviant movement patterns in healthy parts of the body. Making use of the real time muscle force and joint torques visualization can help to sort out the distinction between compensation and primary disorders.

Another example of an application for one embodiment of the present invention is the prevention and treatment of low back pain through teaching of proper lifting techniques. Real-time calculation and visualization of the forces acting on the intervertebral discs will provide immediate feedback to the patient concerning the quality of their movement.

In many embodiments the muscle forces will be visualized, but certain training applications may provide audio signals driven by muscle force values from the computational pipeline. Other training applications may use muscle force values as input for a virtual environment, which causes changes in position of virtual objects, or changes in position of the motion platform on which the subject is standing, The computational pipeline that results in real time muscle force display is flexible and allows forward dynamics simulations to be run at any time during runtime of the system. The flow of movements as an input to the inverse dynamics simulation is stopped during a sequence and the calculated joint movements are now used as input, while the movements become output. Thus forward simulations calculate movements and reaction forces from moments of force produced around the joints of the subjects. These forward simulations can be visualized as part of the virtual environment, and will show what might happen to the patient in hypothetical situations.

The forward and inverse dynamic calculations typically consist of a large set of equations. Depending on the methods used to form these equations, they are expressed in various ways, such as Newton-Euler equations, Lagrange's equations, or Kane's equations. These are called the equations of motion, which contain the relation between the generalized forces applied at the body and the generalized movements. "Generalized" in this respect means that they are formulated along the movement possibilities (or degrees of freedom) of the human body, rather than in terms of three dimensional coordinates in the external world. This implies that most of the generalized forces are actually moments of force (or torque). Equations can be added describing the kind of interaction with the environment, such as contacts with the floor. The equations can be solved simultaneously in a forward simulation, solved algebraically in an inverse simulation or rearranged and solved to do a mixed inverse and forward simulation. In one embodiment of the present invention these computations are all happening in real time.

From the dynamic simulation the location of the center of mass is calculated, which, together with the position of the feet, can be used to drive the motion of the platform, if this is required by the virtual environment. The human body model produces the joint moments of force of the subject. Forward dynamics simulation can be started to indicate where weak parts in the motor pattern are located.

Figure 3:
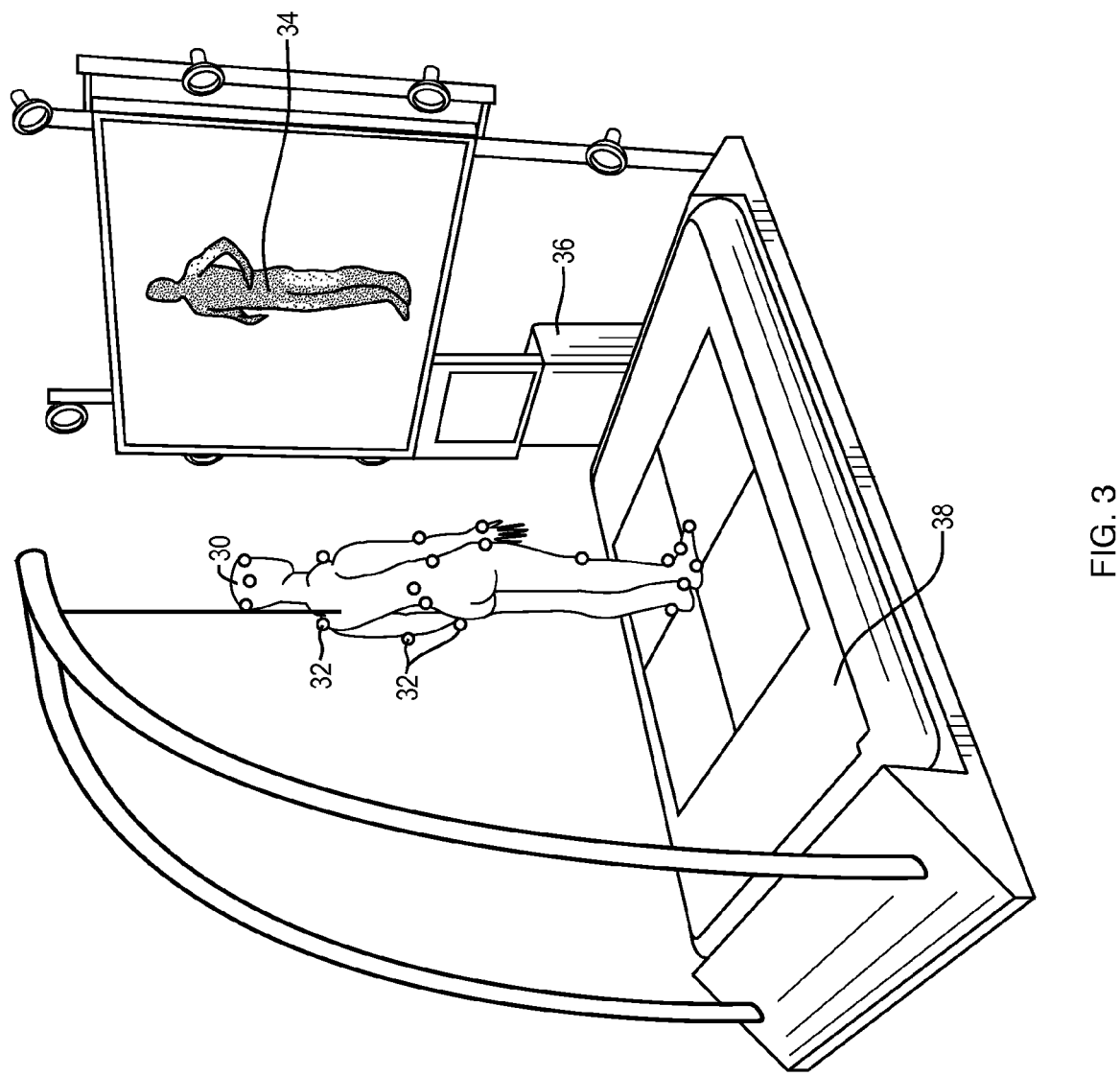
FIG. 3 is a computer generated image illustrating a V-Gait configured in accordance with one embodiment of the present invention, produced by a human figure adorned with optical motion capture sensors standing erect on an instrumented treadmill configured with force sensors and weight sensors, viewing a plasma screen or other video display TV, while being monitored by multiple optical motion capture cameras connected to a control computer running predictive feedback software and generating an image on the TV of a 3D real time interactive muscle model of the human figure.

The main tasks of the real time computational pipeline are processing the input data coming from the motion capture sensors, mapping the collected data into the above mentioned human body model, processing the various input and/or computed data depending on different cases. Other tasks concern the display of real-time 3D graphic representations of muscle forces and joint torques 28, as well as driving the output devices such as a treadmill 38 and a display system 34 as illustrated in FIG. 3.

Figure 1C:
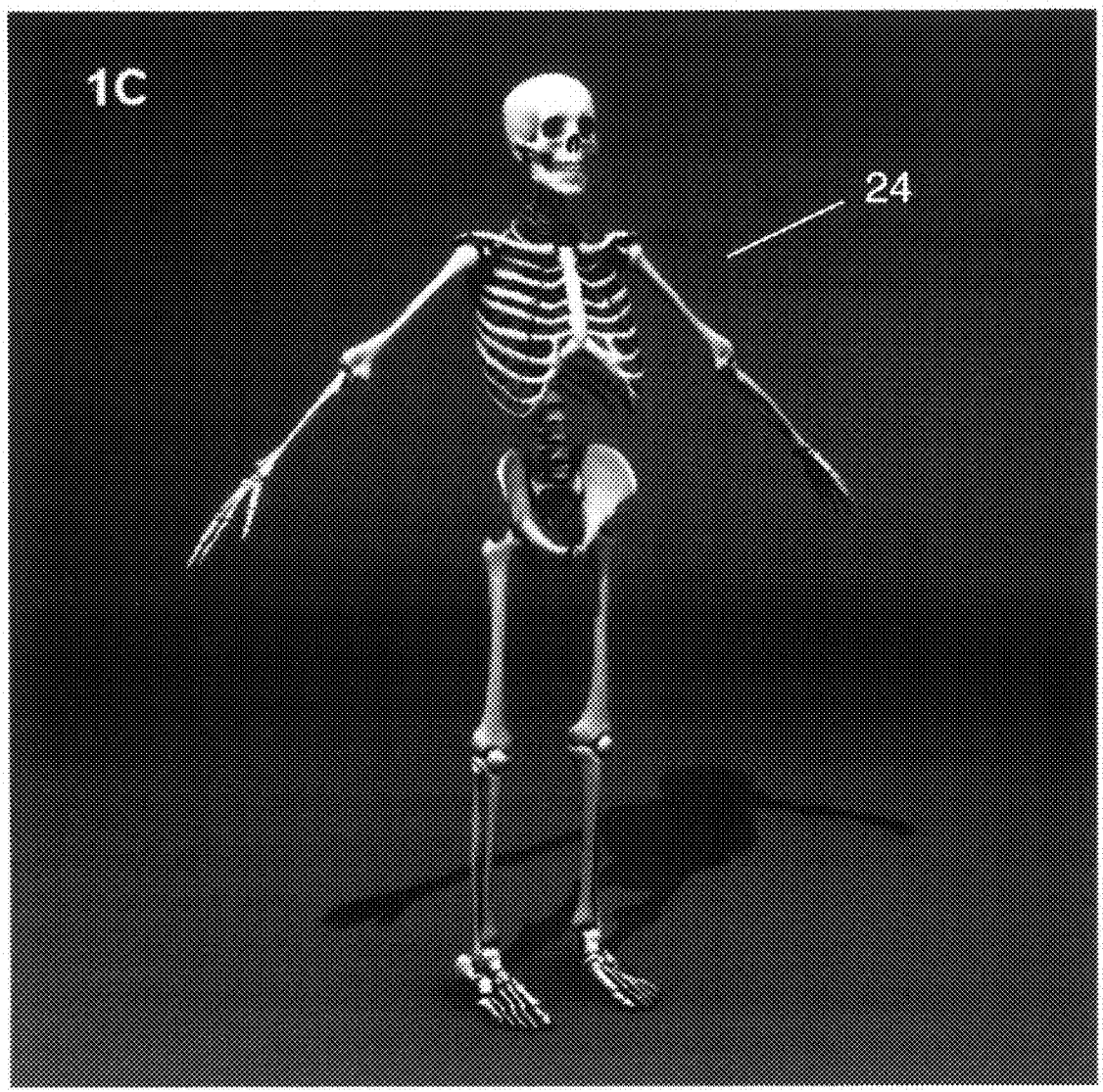
FIG. 1C is a computer generated image illustrating an anatomically correct skeleton configured in accordance with one embodiment of the present invention, in conjunction with the data of FIG. 1.
Figure 1D:
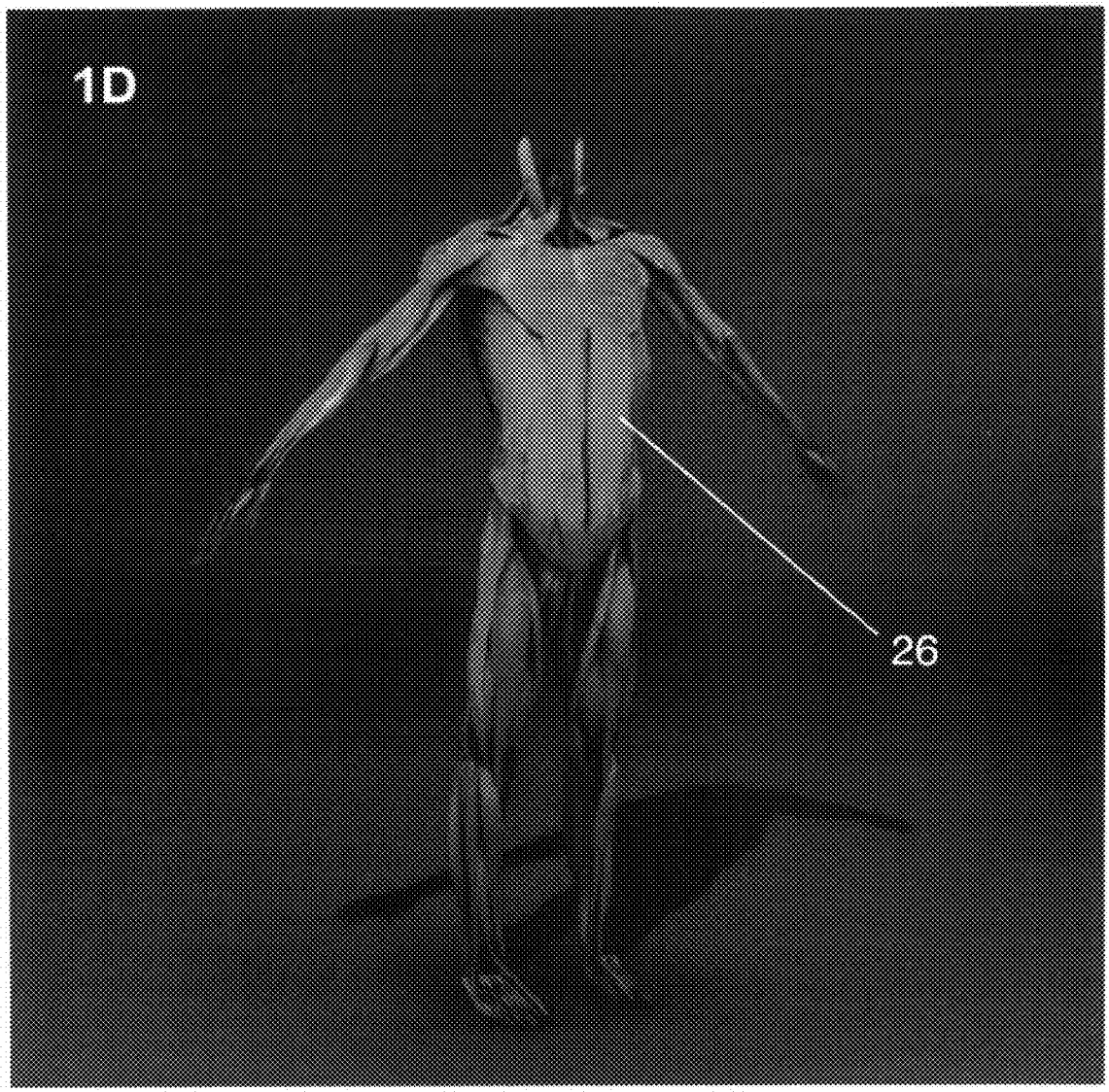
FIG. 1D is a computer generated image illustrating a three dimensional anatomically correct muscle layer configured in accordance with one embodiment of the present invention corresponding with the data set of FIG. 1.
Figure 1E:
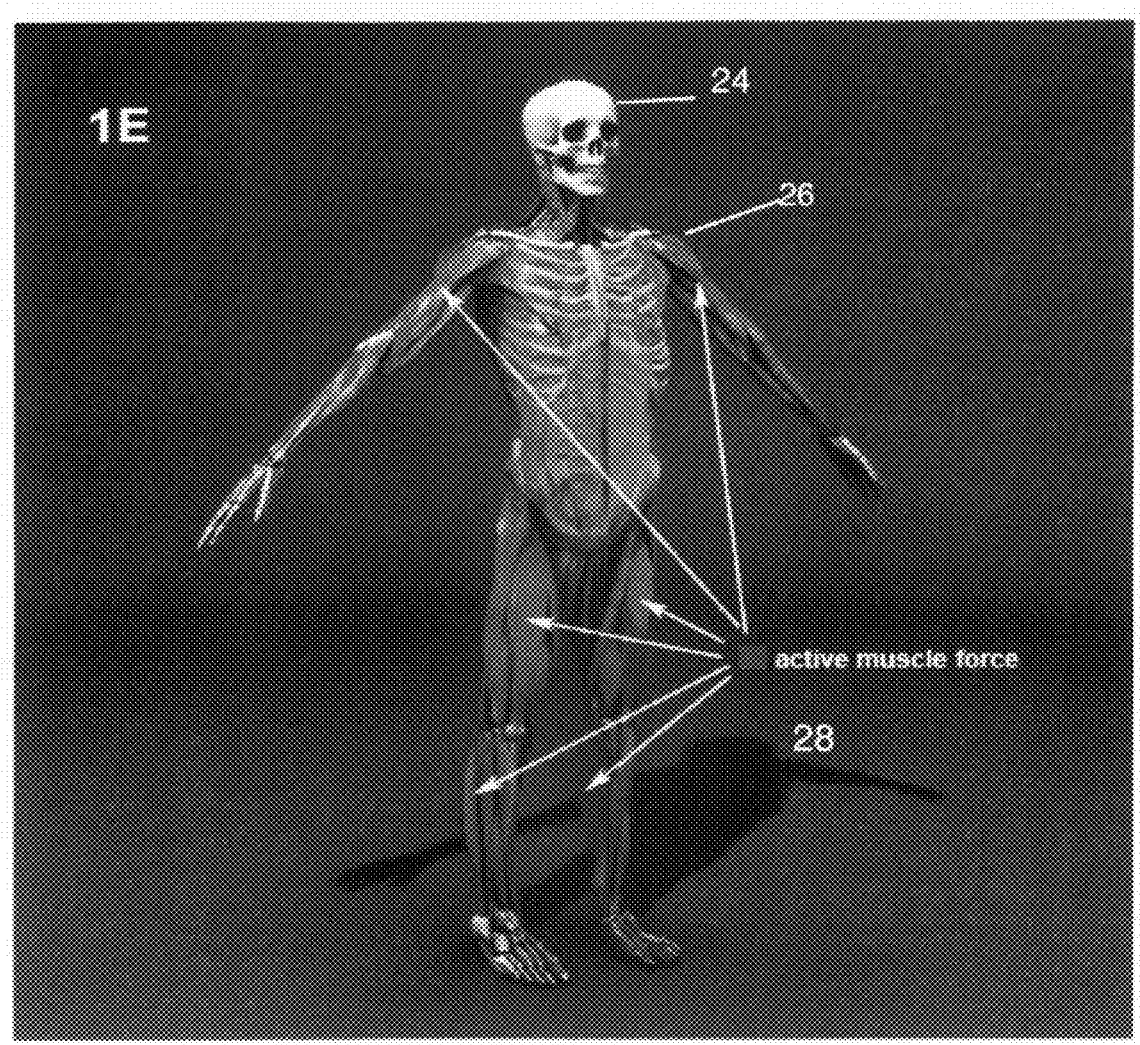
FIG. 1E is a computer generated image illustrating a three dimensional anatomically correct muscle layer disposed on an anatomically correct three dimensional skeleton configured in accordance with one embodiment of the present invention, corresponding to the data points of FIG. 1, where active muscle forces are indicated by color brightness and hue.

The user interface for the operator is implemented as the means to communicate with the real time 3D muscle model 26 of FIG. 1D through a custom written software program. As an example of operation, after having decided on the type of motions to execute, the real time 3D muscle model is projected on the screen in front of the subject, The user stands on a platform or treadmill, which can be controlled as part of the system or as a reaction to movements of the subject. The user wears motion capture markers 20, as illustrated in FIGS. 1A and 2 of which the positions are recorded. These are fed into an algorithm that turns them into the degrees of freedom of the human body model, which is filled with the segment masses 22 and inertia of the subject and displayed as color space real time animations of the 3D muscle model of FIG. 1E.

From the skeleton motion and mass properties, also the location of the center of mass is calculated, which, together with the position of the feet, can be used to drive the motion of the treadmill or platform as required by the environment. The human body model 26 produces the joint moments of force of the subject, if necessary; this information can be offered in the projected image to be used by the subject. Forward dynamics simulation can also be computed to indicate where weak parts in the motor pattern are located.

FIGS. 1A-1E illustrate an overview of one embodiment of the present invention's computational real time pipeline wherein as illustrated in FIG. 1A a user is equipped with a number of motion capture sensors or markers 20 attached at various strategic locations of the body. The data from the sensors is received by a motion capture system 32. In a preferred embodiment, the motion capture data set contains the X axis, Y axis, and Z axis positions of the user for the full body, and is transmitted at >100 FPS (Frames per second) to the computer 36. The computer 36 interactively operates with operator's interface 34 and executes the first step in the computational pipeline converting the positional data in real time to an inverse kinematics skeleton 22 illustrated in FIG. 1B. This data is typically applied to the inverse kinematics skeleton 22 to drive a 3D anatomically correct skeleton 24 in about approximately real time (FIG. 1C). Then a 3D anatomically correct muscle layer 26 of FIG. 1D is connected to the human skeleton 24 and the muscle forces and joint torques resulting from the real time computational pipeline are applied to real time animations of colors 28 of the respective muscles in the 3D muscle model of FIG. 1E.

Referring to FIG. 2, a person is outfitted with markers 20 and a template 22 is processed for an initial or balance position. The markers 20 are typically used to record the motion. They are substantially instantaneously captured, and used to process a complete template. The template 22 utilizes a template matching algorithm to interpolate for missing or bad marker data. The Template matching result is passed to the computational inverse kinematics skeleton 24. Here position data of the markers is plotted in real time to joint orientations in the computational skeleton 24. Using Constraint based rigging; the data is in turn driving a geometry (anatomically correct) skeleton. This skeleton is the base for the muscle force visualization layer.

FIG. 3 illustrates an embodiment of the present invention, comprising a computer-based motion capture system linking a treadmill instrumented with force and weight sensors, multiple optical motion capture cameras and a plasma screen or other video display means to a control computer running predictive feedback software for generating an image on the TV of a 3D real time interactive muscle model of a figure on the treadmill, wherein the patient 30 on instrumented treadmill 38 is looking at the 3D real time interactive muscle model 34 of himself seeing the muscles in action as muscle force is exerted. This interactive muscle force model 34 is calculated by a processor 36 using the method described above using data obtained from optical motion capture sensors 32 disposed on the patient's body 30, in combination with sensors disposed in the instrumented treadmill 38. In one such embodiment, weight sensors may be disposed in the instrumented treadmill 38 while other sensors such as accelerometers, speedometers, rotation and position sensors may also be included.

Figure 4:
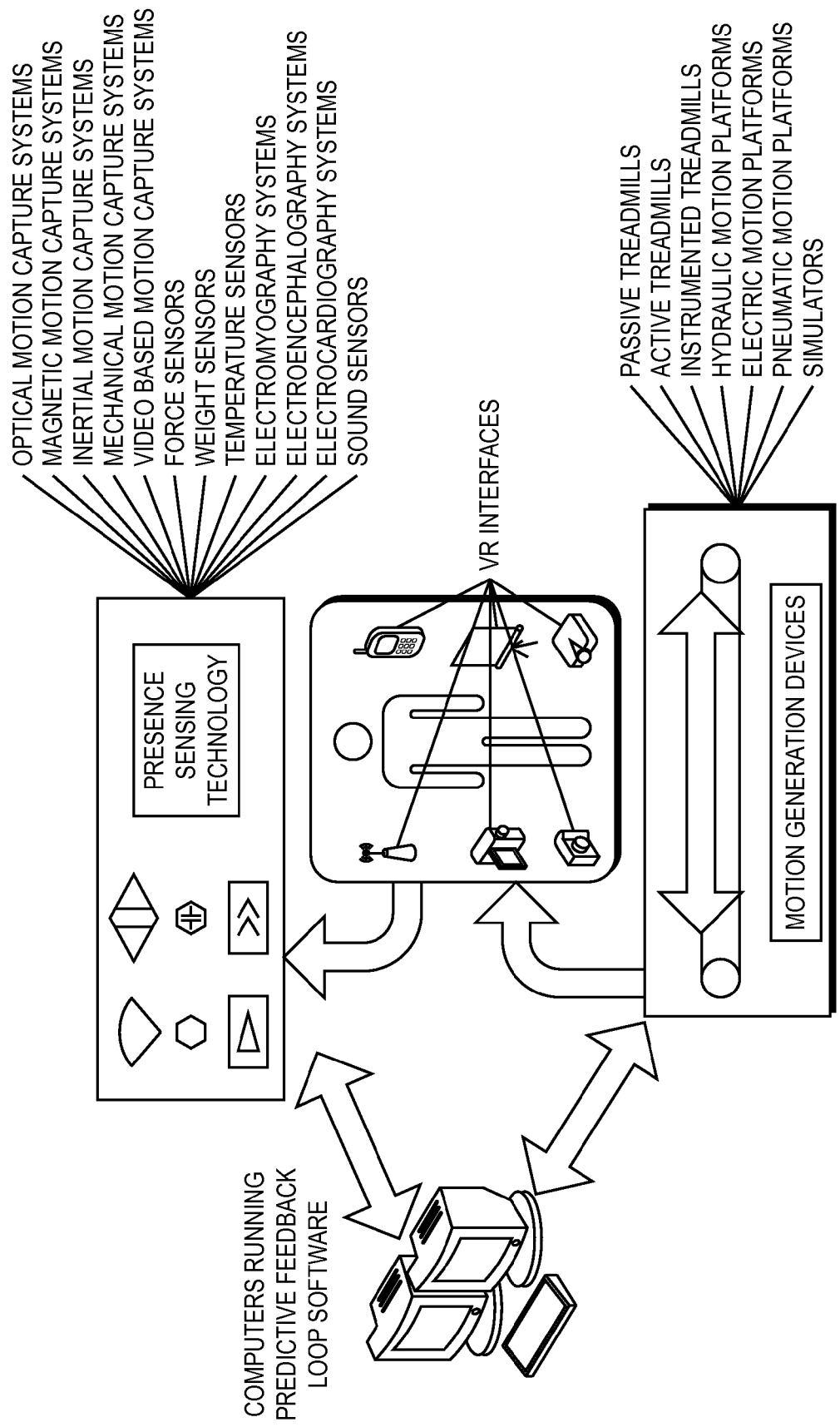
FIG. 4 is a block diagram illustrating a motion capture computer system configured in accordance with one embodiment of the present invention.

FIG. 4 is a block diagrammatic view illustrating the hardware and software elements and possible interconnections of one embodiment of a motion capture system. Computers running predictive feedback loop software are linked to presence sensing technology such as optical motion capture systems, magnetic motion capture systems, inertial motion capture systems, video based motion capture systems, force sensors, weight sensors, temperature sensors, electromyography systems, electroencephalography systems, electrocardiography systems and sound sensors. The computers are also linked to motion generator devices such as passive treadmills, active treadmills, instrumented treadmills, hydraulic motion platforms, electric motion platforms, pneumatic motion platforms, and motion simulators. The presence sensing technology and the motion generation devices are linked by various possible interface devices to the subject. The hardware platform is based on high end multi-core Multi-processor workstations.

Referring to FIGS. 3 and 4, in one embodiment the multi-CPU hardware platform 36 is used as the computer means for processing, memory, and interface. The various peripherals and communications are accomplished by using standard high-speed connections using Ethernet, serial, and SCSI connections to dedicated hosts. The dedicated host can be a separate personal computer (PC) or an integrated on-board computer that interfaces with the peripheral equipment. The optical motion capture system of one embodiment includes six cameras, and the data acquisition unit of the optical motion capture system translates the camera input into the desired data set.

The data set of one embodiment is 3D position information of the sensors 20 obtained from a person 30 in real time, and is accessible to a dedicated host that allows for the fast exchange of data to the CPU 36. Data is, in one embodiment, delivered in a custom made file format. Though not limited to this type of system, the chosen main optical capture system of one embodiment is a realtime passive marker system 32, which is readily configurable for many setups. This technology is capable of converting and displaying 3D data coordinates of up to 300 optical markers at >100 HZ, The instrumented treadmill 38 is interconnected to dedicated host that connects to the CPU for transferring data and control information. The treadmill 38 of one embodiment has the capacity of measurements of real time ground reaction forces by the use of force sensors under the treadmill belt. It's speed is interconnected to the computational pipeline for establishing a feedback loop between the motion capture system 32 and the treadmill 38 so that the person is remaining at the center of the treadmill regardless of changes in the walking/running speeds. A projection device 34 such as a plasma screen or a video projector and screen is used to display the real time 3D muscle model to the user.

Figure 5:
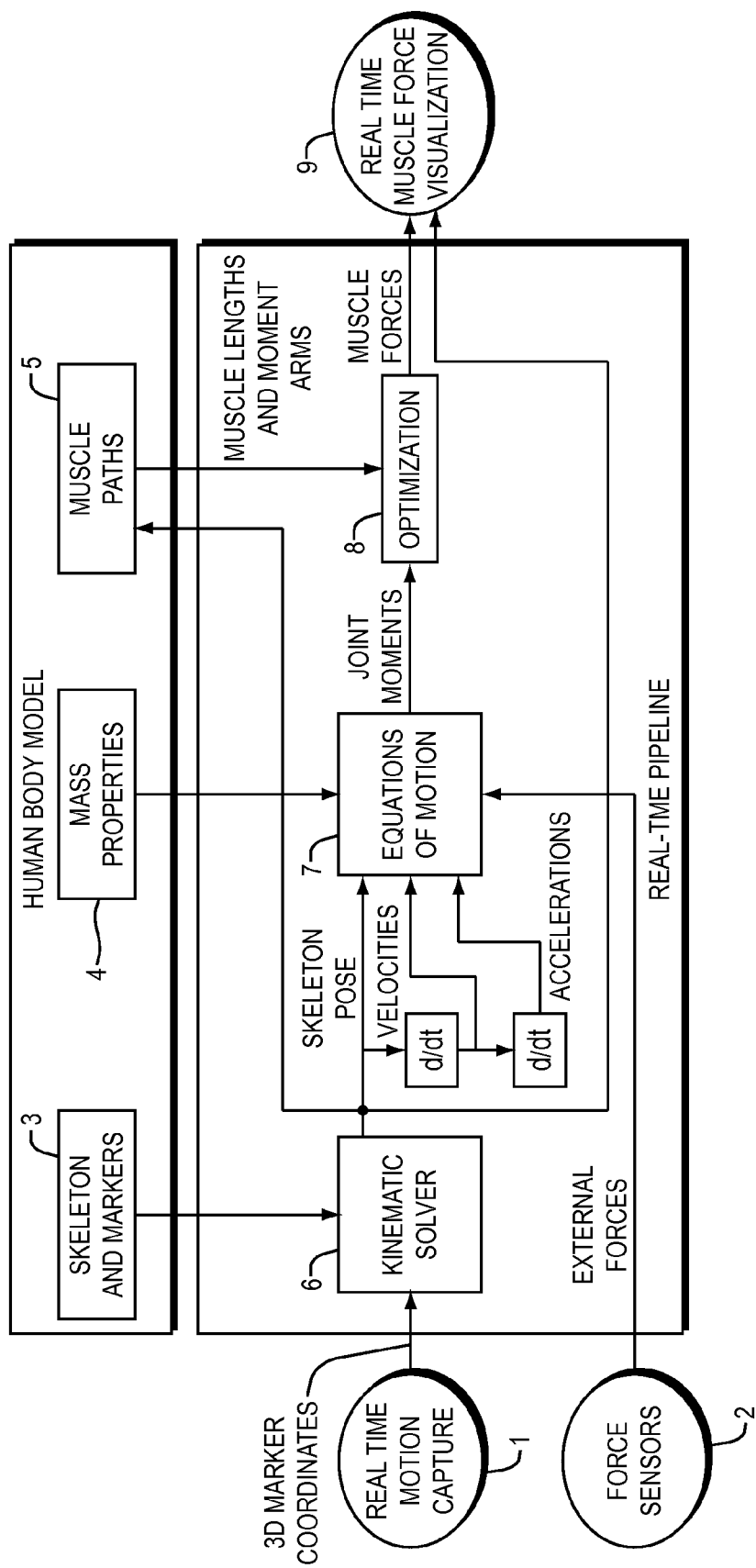
FIG. 5 is a flow chart illustrating a method of motion capture configured in accordance with one embodiment of the present invention.

FIG. 5 illustrates a flow chart illustrating the operation of a system configured according to one embodiment of the present invention for generating real time muscle force visualization of a subject using real time motion capture with force sensors processed through a real-time pipeline utilizing a first human body model lookup table of skeleton and markers configurations, a second human body model lookup table of mass properties, and a third human body lookup table of muscle paths. Input from the motion capture system 1 in the form of 3D marker coordinates is used as input for the Kinematic Solver 6. The Kinematic solver 6 is also using resource files from the first lookup table of a skeleton definition and marker set templates 3. The Kinematic Solver 6 is outputting in real-time the current skeleton pose. Real-time low-pass filtering and differentiation processes the changes in skeleton pose into first and second derivatives of velocities and accelerations that are used as input to the Motion Equations 7. The Kinematic Solver output to the muscle path third lookup table also drives the generation of Muscle paths for all respective muscles 5, and outputs the schematic skeleton used for the visualization 9. The Motion Equations 7 are also using input from ground reaction forces and other external forces coming from an array of Force sensors 2. The Motion Equations 7 also use an input from resource files of the second human body model lookup table that contains the respective body mass properties 4. The Equations of Motion 7 Output Joint moments to the Optimization process 8, The Optimization process 8 also uses input of muscle lengths and moment arms coming from the respective muscle paths 5 from the muscle paths third lookup table. The Optimization process 8 Outputs Muscle forces used in the Real Time muscle force Visualization 9.

In one embodiment of the invention, the skeleton pose (i.e. the set of generalized coordinates) is calculated in real-time by using the Levenberg-Marquardt nonlinear least-squares algorithm to solve the global optimization problem. The use of the analytical Jacobian matrix makes the computations very fast.

In one embodiment of the invention, equations of motion have produced via software that creates C code for the forward kinematics equations. Those equations generate coordinates of markers on the body from the generalized coordinates of the skeleton. The derivatives of the forward kinematics equations, forming a Jacobian matrix, are generated by via symbolic differentiation. Finally, one embodiment of the present invention translates these equations into computer code which is incorporated into the computational pipeline which executes the calculations at run time.

In one embodiment, the muscle forces are the solution of a static optimization problem, with the general form: minimize the sum of normalized muscle forces raised to the Nth power, while requiring that all muscle forces are non-negative, and that the set of muscle forces multiplied by their respective moment arms, are identical to the joint torques solved by the inverse dynamics equations. Normalized muscle force is defined as the muscle force relative to the maximal force capacity of the muscle. Moment arm is the distance from the muscle force vector to the instantaneous center of rotation of a particular joint and is mathematically calculated as the derivative of muscle length with respect to the joint's generalized coordinate. Traditional optimization methods are too slow for real-time applications. For N=2, which is commonly used in muscle force estimation, a solution is obtained in real time using the neural network algorithm for quadratic programming.

Motion Capture is a phrase used to describe for a variety of techniques for capturing the movement of a body or object, and the technology has existed for many years in a variety of applications. The aim of motion capture is to create three-dimensional (3D) animation and natural simulations in a performance oriented manner. In the entertainment industry, motion capture allows an operator to use computer-generated characters. Motion capture is used to create complex natural motion, using the full range of human movements and allow also inanimate objects to move realistically. Some motion capture systems provide real-time feedback of the data and allow the operator to immediately determine whether the motion works sufficiently. Motion capture can be applied to full body motion as well as to hand animation, facial animation and real time lip sync. Motion capture is also used in medical, simulation, engineering and ergonomic applications, and in feature films, advertising, TV and 3D computer games. In the context of the present invention, motion capture is used to output 3D XYZ marker positions.

Force sensors are used in many industries such as Automotive, Robotics and various Engineering applications, typically a force sensor will measure the total forces applied on it, those can be vertical force or horizontal and shear force components. In the context of the present invention, force sensors are used to measure ground reaction forces from the treadmill a person is standing, walking or running on. For example, the treadmill of one embodiment has the capacity of measurements of real time ground reaction forces by the use of force sensors under the treadmill belt, It's speed is interconnected to the computational pipeline for establishing a feedback loop between the motion capture system and the treadmill so that the person is remaining at the center of the treadmill regardless of changes in the walking/running speeds.

Skeleton definition and marker set Templates 3 are resource files used in the computational pipeline of the current invention, people are different in size and weight and a skeleton templates is selected from a group of skeleton templates to get the best match for every person. Marker templates are used to define where the 4 markers are placed on the human body. Typically, such markers are disposed at every joint of the body.

Body mass properties 4 pertains to the weight of different body parts of different people. People vary in weight and this has ramifications on the muscle force they exert to generate specific motions. The mass properties are used as a resource for the correct real time force computations.

Muscle paths 5 are utilized to compensate for differences in build between users. Variations in length and width between subjects have ramifications to the force computations as a longer muscle will exert different force to generate the same motion then a shorter muscle, also the placement of the ligaments will be different in different people. In the context of one embodiment of the present invention, muscle paths are used to assist the computations of muscle forces and joint torques.

Kinematic solver 6 provides for the calculation of joint orientation using inverse kinematics. Kinematics is the process of calculating the position in space of the end of a linked structure, given the angles of all the joints. Inverse Kinematics does the reverse. Given the end point of the structure, what angles do the joints need to be in to achieve that end point? This process is used in robotics, 3D computer animation and some engineering applications. In the context of one embodiment of the present invention it is a single step in the data analysis pipeline, taking the data stream from the motion capture system and calculating the joint angles for every body part. In the context of one embodiment of the present invention, Inverse kinematics is used to calculate the joint orientation from the motion capture data, and to thereby convert XYZ positional data to rotation angle data of the joints in degrees or radians.

Equations used in the calculation of motion and force are known to those skilled in the physical sciences, or are readily derived from equations well known in the field of physics. Motion Equations 7 are sets of mathematical equations designed to combine incoming streams of kinematics data with marker and skeleton templates and convert those to forward and inverse dynamics data. Those can be lagrangeian equation sets, Casey sets, or Euler-Newton equation sets. In the context of one embodiment of the present invention, the motion equations 7 provide the relationship between generalized forces applied at the body and generalized movements. "Generalized" in this respect means that they are formulated along the movement possibilities (or degrees of freedom) of the human body, rather than in terms of forces in the external world. This implies that most of the generalized forces are actually moments of force (or torque). Equations 7 can be added describing the kind of interaction with the environment, such as contacts with the floor. The equations 7 can be solved simultaneously in a forward simulation, solved algebraically in an inverse simulation or rearranged and solved to do a mixed inverse and forward simulation. In one embodiment of the present invention these computations are all happening in real time. In one embodiment, effective delay is eliminated using efficient algorithms, achieving a minimal sampling speed in real time to be greater than 30 hz, a standard familiar to those in the television and broadcast industries. One skilled in the art will readily appreciate that faster time would likewise be acceptable or desirable in some applications.

An optimization process 8 uses the input of muscle lengths and moment arms coming from the respective muscle paths to output muscle forces and joint torques. The optimization 8 of the data contains routines for data normalization and several real time software filters Real Time muscle force visualization 9 is provided by inputs of muscle forces and joint torques and are used to drive color animation on the respective muscles displayed as a 3D human body model on screen. The color brightness and hue correlates with the muscle force amplitude, gain and activation patterns. The user and operator can see a real time animation of the muscle forces active in the human body at any given time Various embodiments of the present invention provide applications adaptable for other market segments. Sports and fitness is one such market. One embodiment of the present invention provides a tool that is useful in numerous applications, including the fitness industry. This system allows the visualizations of muscle forces for any given exercise in real-time. The system can be used to enhance and improve muscle forces, by providing a realistic visualization of the given forces and torques. The present system allows the user to see the force transference to various muscles in the body and achieve a desired effect. The motion capture system instantly records the user's motion and provides immediate muscle force visualizations.

One embodiment of the present invention may have an enormous impact in the medical community by making it possible to view muscle forces and torques in real-time. It can assist and improve the quality of life of many patients and allow the perception of physical movement and muscle behaviors for those not otherwise capable of such motion. The system is useful for victims of traumatic brain injury, cerebral damage, and spinal damage. The study of motion recognition supports the notion that the body remembers certain movements and can even regenerate synoptic paths. By visualizing the desired muscle force, the body can be re-trained to make that movement. In the field of orthopedics and prosthetics, the present invention can assist patients in understanding their present situation, where they lack muscle force and where they are exerting too much force for compensation reasons. With orthopedics, prosthetics, and amputees, the system can visualize and track muscle deficiencies while training and improving movements. One embodiment of the present invention in relation to medical applications can serve as an example. One development project called "Virtual Gait Lab" is one embodiment of the system operating in the real-time domain. This project pertains to the development of a virtual reality system in which the muscle forces and joint torques of the human body can be seen and evaluated in real time in a variety of reproducible conditions. One of the major objectives of such a project is to enhance diagnostic and therapeutic activities in a range of medical fields. The enhancements are defined by allowing a medical expert team for the first time the opportunity to view and analyze muscle forces and joint torques patterns as they happen in a controlled real-time environment.

In one embodiment such as that illustrated in FIG. 3, the system consists of a combination of an instrumented treadmill 38 that is capable of measuring ground reaction forces, a large screen or projection system for the display of the forces 34, real time motion capture system 32 and the custom computational pipeline 36 translating the capture data to muscle forces and joint torques display.

Various embodiments of the present invention seek to develop an interactive virtual real-time muscle model, which can provide patients with means of almost unlimited exploratory behaviors and at the same time provide medical experts accurate measurement tools for monitoring the complex array of forces present in the human body. Especially in complex balance tasks, the patterns of muscle activation determine whether a subject falls or not. These simulations are aimed at an understanding of normal or pathological response patterns in certain balance tasks. Such an embodiment offers not only a test- and learning environment for patients and doctors, but is also a valuable research environment for motor control. Such an embodiment opens the door to a new type of experiments in which real time muscle force visualization can be offered. For example the muscle force tremors as observed in Parkinson patients are considered to be an enigma by many clinicians and human movement scientists. In these patients some visual cues are sufficient to trigger rather normal looking muscle force patterns (for instance used in walking), while in the absence of such stimuli a pattern can not even be started. In healthy subjects, the continuous control of muscle force transference during walking is possible by having a multi-channel sensory input onto a vast library of learned motor patterns. Once the possibility exists to view in real time the muscle force pattern immergence, it will lead to fundamental improvement in the understanding and possible treatment of the sickness. Such an embodiment will allow a new glimpse into the complexity of the natural processes associated with human motion. Other examples can be found among patients with peripheral disorders, such as partial paralysis or paresis of a limb. In these situations, gait and balance are compromised both by a partial lack of sensory input and a lack of muscle coordination. The usual result of that is that in order to obtain a functional gait and balance the patients find compensations, resulting in deviant movement patterns in healthy parts of the body. Making use of the real time muscle force and joint torques visualization can help to sort out the distinction between compensation and primary disorders.

One embodiment of the invention is a new principle in real time visualization, where muscle force is seen and evaluated in a totally new way. This principle establishes a mechanism to achieve a visualization state whereby the persons involved can see immediately which muscles they are using and to what extent.

One embodiment of the present invention is a muscle force processing system, comprising a processing means, a motion capture system connected to the processing means. The motion capture data is taken from a plurality of motion sensors and is processed in real-time. There is a computational pipeline connected to the processing means, wherein resulting data is also processed in real-time, and wherein resulting data is visualized in real time through color space changes in a 3D muscle model showing the muscle forces and joint torques in real time. There is also a means of interfacing to the muscle model with a runtime control input. A further embodiment is an instrumented treadmill capable of measurements of ground reaction forces, wherein the measurements of said ground reaction forces are integrated in the computational pipeline resulting in real time view of muscle forces and joint torques. A further embodiment is a 3D interactive muscle model further comprising an inverse kinematics skeleton layer, a 3D geometry anatomically correct skeleton layer and an anatomically correct muscle model layer. An additional embodiment is a real time computational pipeline, further comprising a memory means for recording the motion capture data and processing the data in real time through the said layers of the processing real time pipeline. Another embodiment is a method and system for real time visualization registration, evaluation, and correction of muscle forces and joint torques in the human body, wherein the full process is happening in real time.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A method for computing, measuring, recording and viewing in real time muscle forces and joint moments of a body in motion, employing a system for visual display and output of anatomical forces, said system comprising:
    a motion capture system for collecting and recording real time position data;
    a computer receiving data from said motion capture system and deriving rotational data therefrom;
    a first look up table comprising biomechanical body skeleton definition and marker set templates, a second look up table comprising body mass properties, and a third look up table comprising muscle paths;
    a computational pipeline disposed on said computer; and
    a computer display unit for displaying color animation,
    said method comprising:
    placing the body in motion within range of the motion capture system;
    collecting and recording in real time three dimensional coordinates of selected marker points on the body in motion;
    calculating in real time a skeleton pose of the body in motion from the three dimensional coordinates and from said first look up table;
    calculating in real time joint moments of the body using the skeleton pose of the body in motion, a first derivative velocity of the skeleton pose, a second derivative acceleration of the skeleton pose, force vectors representing external forces affecting the body in motion, and body mass properties from said second look up table;
    calculating in real time muscle lengths and muscle moment arms using the skeleton pose and said third look up table;
    calculating in real time muscle forces using the joint moments, muscle lengths and muscle moment arms, by using quadratic programming and a neural network optimization algorithm for said quadratic programming; and
    generating and displaying in real time from the calculated muscle forces while the body in motion remains in motion, a color animation of a muscle model whereby a relative degree of muscle force of the body in motion is displayed by a relative coloring of the respective muscles of the color animation.

2. The method of claim 1, wherein said color animation of a muscle model further comprises joint moments presented by scale and color of three dimensional vector animations.

3. The method of claim 1, further comprising:
    placing at least one motion capture marker on said body defining said three dimensional coordinates;
    collecting and recording real time positional data from said at least one marker; and
    deriving rotational data from said at least one of the motion capture markers.

4. The method of claim 1, wherein said body in motion is a human body, and said color animation is being displayed to said body in motion in real time as visual feedback.

5. The method of claim 1, wherein said motion capture system comprises sensors for said collecting and recording of real time position data, the sensors selected from the group of sensors consisting of optical, magnetic, inertial, and video based sensors.

6. The method of claim 1, wherein said system for visual display and output of anatomical forces comprises an instrumented platform supporting said body in motion.

7. The method of claim 2 wherein said muscle forces and said joint moments are displayed on a representation of a human body.

8. The method of claim 4, further comprising:
    selecting a biomechanical body skeleton definition and marker set template approximating a build of the human body.

9. The method of claim 1, wherein said computation pipeline comprises use of a Jacobian matrix to facilitate said computing in real time.

10. A method for viewing in real time muscle forces and joint moments of a body in motion employing a system for visual display and output of anatomical forces, said system comprising:
    a motion capture system for collecting and recording real time position data;
    a computer receiving data from said motion capture system and deriving rotational data therefrom;
    a first look up table comprising biomechanical body skeleton definition and marker set templates, a second look up table comprising body mass properties, and a third look up table comprising muscle paths;
    a computational pipeline disposed on said computer; and
    a computer display unit for displaying color animation;
    said method comprising:
    placing a body in motion within range of said motion capture system;
    calculating in real time a skeleton pose of the body in motion from three dimensional coordinates of selected marker points on the body in motion and from said first look up table;
    calculating in real time joint moments of the body in motion using the skeleton pose of the body, a first derivative velocity of the skeleton pose, a second derivative acceleration of the skeleton pose, force vectors representing external forces affecting the body in motion, and body mass properties from said second look up table;
    calculating in real time muscle lengths and muscle moment arms using the skeleton pose and said third look up table;
    calculating in real time muscle forces of the body in motion using the joint moment, muscle lengths and muscle moment arms, and optimization algorithms;

generating and displaying in real time from the calculated muscle forces a color animation of a muscle model whereby a relative degree of muscle force of the body in motion is presented by relative coloring of the respective muscles in the color animation; and having an operator interact with the system during system runtime.

* * * * *